(12) United States Patent
Burg et al.

(10) Patent No.: US 6,747,009 B2
(45) Date of Patent: Jun. 8, 2004

(54) PEPTIDOMIMETIC GLUTATHIONE ANALOGS

(75) Inventors: Danny Burg, Voorschoten (NL); Gerard Johan Mulder, Oegstgeest (NL)

(73) Assignee: Universiteit Leiden, Leiden (NL)

( * ) Notice: Subject to any disclaimer, the term of this patent is extended or adjusted under 35 U.S.C. 154(b) by 0 days.

(21) Appl. No.: 10/246,424

(22) Filed: Sep. 19, 2002

(65) Prior Publication Data

US 2004/0063640 A1 Apr. 1, 2004

(51) Int. Cl.[7] ............................................. A61K 38/00
(52) U.S. Cl. ............................ 514/19; 514/19; 514/2; 530/323; 530/333; 530/335; 530/336; 530/337
(58) Field of Search ............... 514/19, 2; 530/300, 530/323, 335–337, 532

(56) References Cited

FOREIGN PATENT DOCUMENTS

EP          1 072 608 A1   *  1/2001

\* cited by examiner

Primary Examiner—Christopher R. Tate
Assistant Examiner—B. Dell Chism
(74) Attorney, Agent, or Firm—Sughrue Mion, PLLC

(57) ABSTRACT

The invention relates to peptidomimetic compounds with formula

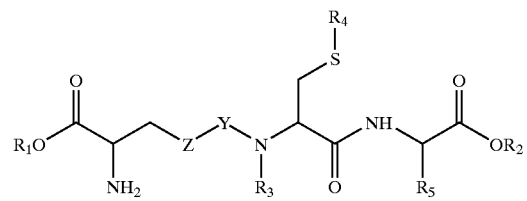

wherein $Z=CH_2$ and $Y=CH_2$, or $Z=O$ and $Y=O=O$, which are novel analogs of glutathion and are inhibitors of glutathione S-transferase, in particular of GST P1-1. Such inhibition has beneficial effects in therapy against cancer. In particular compounds in which $R_3$ is H, $R_4$ is benzyl and $R_5$ is phenyl are stable towards γGT activity and are selective for GST P1-1.

8 Claims, 4 Drawing Sheets

PEPTIDOMIMETIC GLUTATHIONE ANALOGS

FIELD OF THE INVENTION

The invention relates to peptidomimetic compounds which are novel analogs of glutathione. The invention also relates to pharmaceutical compositions comprising such glutathione analogs. The novel analogs are useful as inhibitors of glutathione S-transferase, in particular of GST P1-1. Such inhibition has beneficial effects in chemotherapy.

BACKGROUND OF THE INVENTION

The tripeptide glutathione (GSH), γ-glu-cys-gly, plays a critical role in the cellular protection against potentially harmful electrophiles from xenobioytic sources or those generated by endogenous oxidative processes. GSH-conjugates are formed by nucleophilic attack of the cystein sulfhydryl on the electrophilic center of a suitable substrate. This process is catalysed by glutathione-S-transferase (GST). Several members of the GST-isoenzyme family are involved in conjugation of drugs and thereby in drug resistance. GST inhibitors may be used to improve drug response and decrease drug resistance. In particular isoenzyme selective GST inhibitors may be of use. Conjugates of GSH and their cell-permeable esterified derivatives are effective competitive inhibitors of GST.

WO95/08563 discloses tripeptide compounds which are analogs of GSH. They are generally inhibitors of GST-activity and the various compounds contained in this group show diverse specificities with respect to GST-isoenzymes. Disclosed are symmetrical esters of 1 to 10C units, with the diethyl ester as the preferred embodiment. In WO00/44366 essentially the same compounds are used, in this disclosure however lipid formulations of diesters with a greater lipophilicity than the corresponding diethylester are preferred. WO95/09866 discloses the tripepitide analogs of GSH modified on the cysteine thiol groups with cytotoxic compounds, in particular phosphorodiamidate. The contents of WO95/08563, WO00/44366 and WO95/09866 are incorporated herein by reference.

GST isoenzymes are classified in a single microsomal subclass and three cytosolic subclasses α, μ and π. These classes show differences in structure, immunological activity, substrate specificity and inhibitor sensitivities.

The GST π isotype has been associated with tumors, including cancers of the colon, stomach, pancreas, uterine cervix, renal cortex, adenocarcinoma of the breast and lung, nodular small cell lymphoma, mesothelioma, small cell and non-small cell lung carcinoma and bladder carcinoma as well as in chronic lymphocytic leukemia (CLL). In particular the enzyme GST P1-1 is over-expressed in many types of human cancers. Elevated GST P1-1 levels also are correlated with the development of resistance to many commonly used chemotherapeutic drugs.

Myelodysplastic syndrome (MDS) is a bone narrow disorder characterized by abnormal production of white blood cells. Animals that lack GST P1-1 activity exhibit higher than normal levels of white blood cells, suggesting that inhibition of the GST P1-1 activity might cause a similar effect. Simulation of white blood cell production by inhibition of GST P1-1 may provide the basis for a treatment of MDS as well as for other hemoatologic conditions associated with low white blood cell levels.

A disadvantage of the known GSH conjugates is their sensitivity towards peptidase-mediated breakdown which results in loss of inhibitory action of the conjugates. Enzymatic cleavage hampers or even obstructs therapeutic use of GSH conjugates. In particular the γ-glutamyl-cysteine peptide bond in the GSH conjugates is sensitive towards γ-glutamyl transpeptidase (γGT).

SUMMARY OF THE INVENTION

It is an object of the present invention to provide metabolically stable GST inhibitors. It is in particular the object to provide compounds that are stable towards enzymatic breakdown or cleavage.

A further objective is to provide GST isoenzyme selective inhibitors, in particular selective for the GST π subclass.

Surprisingly it has been found that compounds as defined in the appending claims meet these objectives. Thus the invention relates to a compound of formula

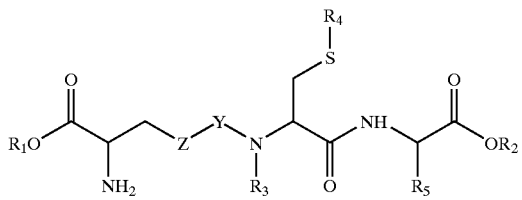

wherein
$Z=CH_2$ and $Y=CH_2$, or
$Z=O$ and $Y=C=O$,
$R_1$ and $R_2$ are independently selected from group consisting of H, linear or branched alkyl (1–25C), aralkyl (6–26C), cycloalkyl (6–25C), heterocycles (6–20C), ethers or polyethers (3–25C), and where $R_1$–$R_2$ together have 2–20C atoms and form a macrocycle with the remainder of formula I;
$R_3$ is selected from the group consisting of H and $CH_3$,
$R_4$ is selected from the group consisting of 6–8C alkyl, benzyl, naphthyl and a therapeutically active compound, and
$R_5$ is selected from the group consisting of H, phenyl, $CH_3$ and $CH_2$phenyl or a pharmaceutically acceptable salt thereof.

In a preferred embodiment $R_3$ in the formula above is H. In a further preferred embodiment $R_4$ in the formula above is benzyl. In yet a further preferred embodiment $R_5$ in the formula above is phenyl.

Further the invention relates to the compound of formula

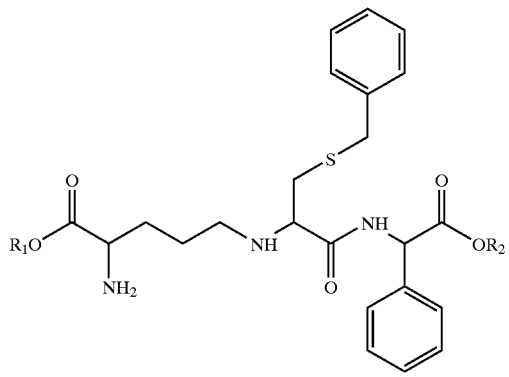

wherein
$R_1$ and $R_2$ are independently selected from the group consisting of H, linear or branched alkyl (1–25C), aralkyl (6–26C), cycloalkyl (6–25C), heterocycles (6–20C), ethers or polyethers (3–25C), and where $R_1$–$R_2$ together have 2–20C atoms and form a macrocycle with the remainder of formula I; or a pharmaceutically acceptable salt thereof.

And further the invention relates to the compound of formula

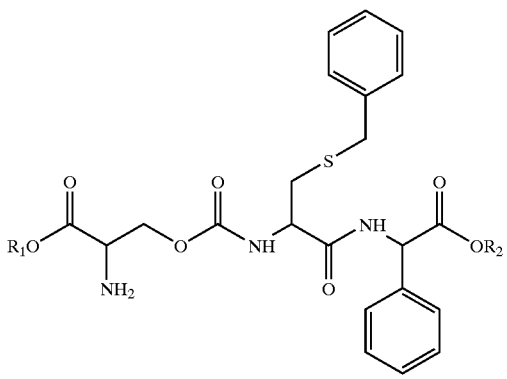

wherein $R_1$ and $R_2$ are independently selected from the group consisting of H, linear or branched alkyl (1–25C), aralkyl (6–26C), cycloalkyl (6–25C), heterocycles (6–20C), ethers or polyethers (3–25C), and where $R_1$–$R_2$ together have 2–20C atoms and form a macrocycle with the remainder of formula I; or a pharmaceutically acceptable salt thereof.

Preferably the peptidomimetic compounds of the invention have the stereochemistry depicted in formula

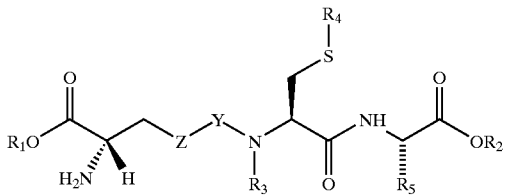

Also the invention concerns pharmaceutical compositions comprising a compound of the above formulas.

The invention also relates to a method for the treatment of cancer in which a peptidomimetic compound according to this invention is used.

DESCRIPTION OF THE INVENTION

Figure 1:
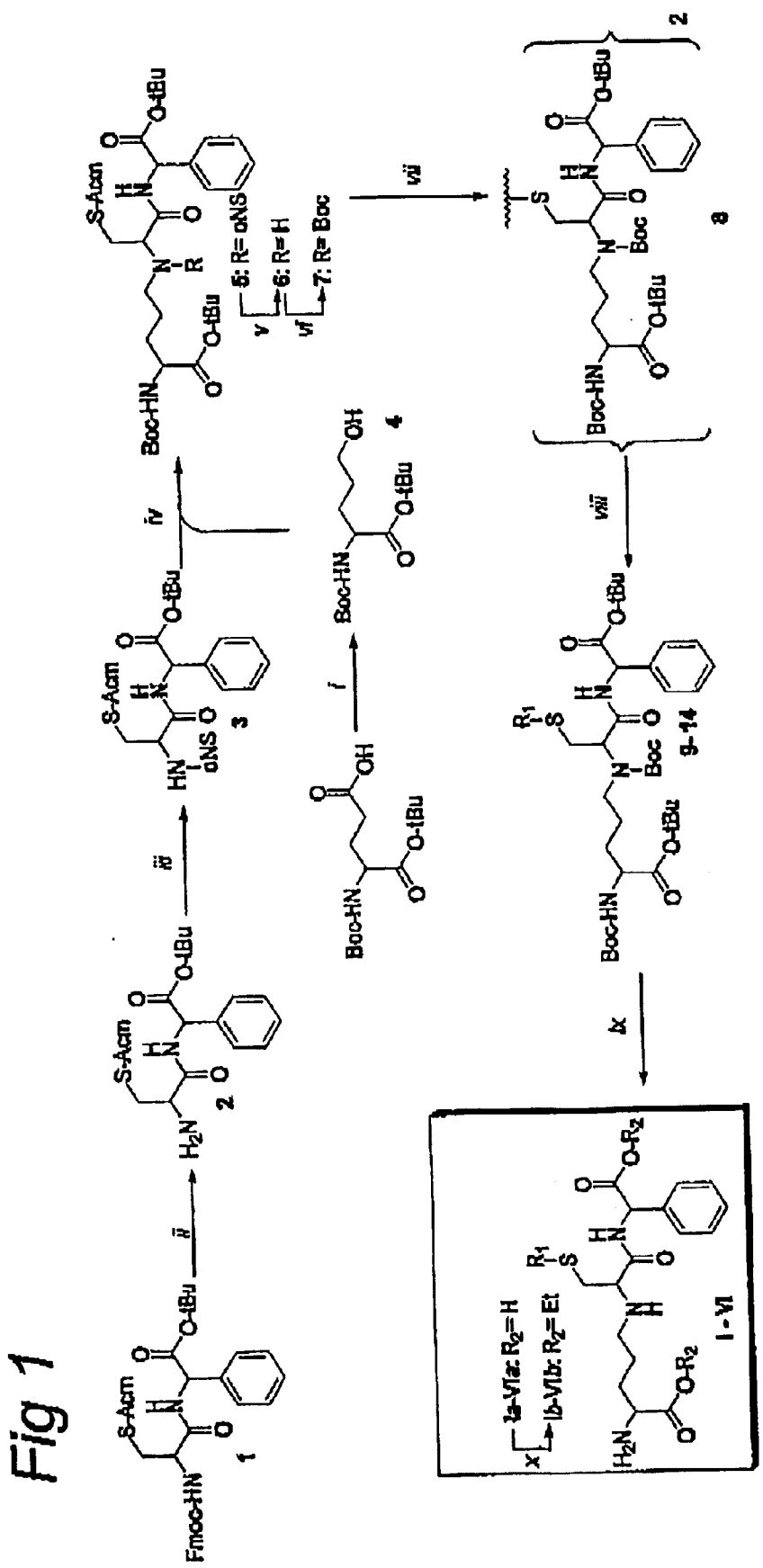
FIG. 1 (scheme 1) represents the synthesis of the 'reduced' peptide isostere, conditions: (i) isobutylchloroformate, triethylamine, NaBH$_4$, THF/H$_2$O, $-40 \rightarrow 0°$ C.; (ii). DBU, DCM; (iii). nitrobenzenesulfonylchloride, DiPEA, CDM; (iv). 4, triphenylphosphine, DIAD, THF; (v). thiophenol, DiPEA, DMF; (iv). Boc$_2$O, DiPEA, MeCN; (vii). I$_2$, MeOH; (viii), tri-n-butylphosphine, nPrOH/H$_2$O, R-Br or α,β-unsat. Ketone; (ix). TFA/H$_2$O (98:2, v/v); (x). SOCl$_2$, EtOH.

This invention relates to novel GST inhibitors, in particular to inhibitors that show selectivity towards GSTP1-1. The new inhibitors partially reverse thiotepa resistance of mammary carcinoma cells that overexpress GSTP1-1, and also modulate the activity of JNK, which has a prominent role in signal transduction cascades. The advantage of these compounds over TER199, the only available comparable inhibitor, is that our compounds are stable towards γGT. TER199 is the diethylester derivative of THR117 which is γ-L-glutamyl-L-cysteinyl(benzyl)-D-phenylglycine (GluPhg-Benzyl), see the examples and table 1. In this description the usefulness of the GST inhibitors in vivo is demonstrated for the diethylesters of the peptidomimetic analogs of this invention and at present this forms the preferred embodiment. However, it is well within the reach of the skilled person to vary the ester groups R1 and/or R2 in the compounds of the invention and determine the respective efficacy.

The γGT-stable GSH analogues of this invention contain an urethane or a 'reduced' amide. From this GSTP1-1 inhibitors are developed that are stable in vivo. Incorporation of a phenylglycine moiety increases their selectivity towards GSTP1-1. The cysteine thiol function of the reduced isostere is coupled to a small series of lipophilic groups to target the H-site of GSTP1-1. The lipophilic group is selected from 6–8C alkyl, benzyl, naphthyl and a therapeutically active compound. Of selected compounds membrane permeable diethyl ester derivatives are prepared to evaluate the effects of GSTP1-1 inhibition in intact cells.

The non-esterified compounds are competitive inhibitors towards GSH of GSTA1-1, GSTM1-1 and GSTP1-1, and therefore most likely interact with the GST active site. The preferred inhibitors show preference towards GSTP-1-1, and are approximately equally potent (see examples table 1). During synthesis, racemization of the phenylglycine moiety occured, as determined by NMR analysis. All compounds are therefore mixtures of R(−)- and S(+)-phenylglycine diastereomers. The absolute configuration of the phenylglycine residue is important for GSTP-1 inhibition; the R(-) diastereomer of phenylglycine containing GSH-analogues is usually several orders of magnitude stronger GSTP1-1 inhibitor than the S(+) diatereoisomer. The inhibitory potency of the compounds, determined by their $K_i$ values, is therefore an underestimation of their real efficiency. Furthermore, since GSTP1-1 is more sensitive towards the absolute conformation of the phenylglycine moiety than GSTA1-1 and GSTM1-1, selectivity may also be better than table 1 discloses. It is well within the reach of the skilled person to develop a a steroselective synthesis for the inhibitors according to this invention, in particular a route in which the racemization of the phenylglycine moiety is prevented. The structure below represents the compounds in their preferred stereoselective conformation.

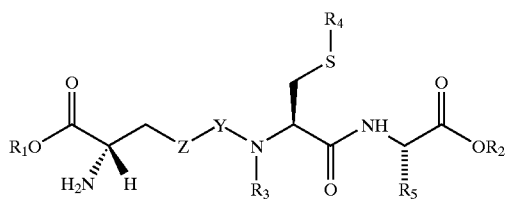

To evaluate the effects of GSTP1-1 inhibition in cells, the VCREMS cell is used line, which has been extensively used to investigate the regulation of GSTP1-1 gene expression. This vincristine resistant MCF7-derived cell line is cross resistant to doxorubicin and etoposide, but not to cisplatin. While MCF7 cells have a very low GSTP1-1 expression, VCREMS cells display strongly elevated levels of GSTP1-1 in the absence of gene amplification. Elevated GSTP1-1 expression in these cells is the result of altered transcriptional mechanisms. To evaluate the GST inhibitors in another GSTP1-1 overexpressing cell line, MTLn3 cells are transiently transfected with GSTP-1-1. Parent MTLn3cells have substantial levels of endogenous π-class GST. After transfection, these cells display approximately 10-fold higher GST activity than mock transfected MTLn3 cells. Western blotting shows that GSTP1-1 levels in MTLn3/ GSTπ was comparable to VCREMS.

Thiotepa is used as model drug to evaluate the effects of GSTP1-1 inhibition on reduction of cell proliferation by alkylating agents. The aziridine moiety of thiotepa is substrate for GSTP1-1, as well as for GSTA1-1. Thiotepa can therefore directly be conjugated to GSH by GSTP1-1. VCREMS cells display increased resistance to thiotepa compared to parent MCF7 cells, which may be a result of their elevated GSTP1-1 expression; VCREMS cells also contain p-glycoprotein, but this has not been shown to transport thiotepa. The GSH-conjugate of thiotepa can be transported by MRP,1 but this membrane transporter is not present on VCREMS cells. Both MTLn3 cell lines were much more sensitive to thiotepa than MCF7 cells. GSTP1-1 transfection only slightly increased thiotepa cytotoxicity in MTLn3 cells.

In all cell lines, the GSTP1-1 inhibitors are equipotent modulators of thiotepa cytotoxicity. GSTP inhibition strongly reduces thiotepa resistance of VCREMS cells. Potentiation of thiotepa cytotoxicity may be explained by inhibition of thiotepa conjugation, yet other mechanisms may also play a role: although MCF7 cells have a very low GSTP and GSTA expression, thiotepa cytotoxicity is also increased in MCF7 cells by co-exposure to the GSTP inhibitors. The GSTP inhibitors may therefore also affect other enzyme systems that play a role in drug sensitivity, such as glyoxalase I, DNA dependent protein kinase (DNA-PK) or members of the MRP family of membrane transporters.

In addition to their action on drug resistance, the GSTP inhibitors also have an effect on GSTπ modulated signal transduction cascades. According to the current understanding of JNK regulation, binding of a substrate or inhibitor to GSTP1-1 induces a conformational change in the enzyme, which then dissociates from JNK and multimerizes, JNK subsequently gets activated and resumes its phosphorylation of downstream substrates. In neo and GSTπ transfected MTLn3 cells, these mechanisms are clearly triggered by exposure to the GSTP1-1 inhibitors. The JNK activation closely correlates with the oligomerization status of GSTP1-1. In MTLn3 cells, JNK activation occurs simultaneously with GSTP1-1 multimer formation. This is in agreement with the previously proposed mechanism for JNK regulation by GSTP1-1. Surprisingly, the GSTP inhibitors have no effect on the GSTP1-1/JNK system in the VCREMS cell line. GSTP1-1 oligomers are observed even in absence of inhibitors, which coincides with the presence of active JNK. A slight increase in GSTP1-1 oligomerization and JNK phosphorylation after exposure of VCREMS cells to the GSTP1-1 inhibitors is observed.

Because the GSTP1-1 inhibitors partially reverses thiotepa resistance of VCREMS cells, it may be concluded that GSTP1-1 is a major contributor to the MDR phenotype of these cells. JNK activity, however, is not affected by the GSTP1-1 inhibitors, which indicates that GSTP1-1 is not crucial for the regulation of the stress kinase pathway in VCREMS cells.

The new inhibitors provide new possibilities to explore GSTP1-1 function in vivo, using the MLn3 tumor model. Furthermore, the GSTP1-1 inhibitors can be used in cancer treatment to potentiate cytostatic drug action and as small molecule myelostimulant.

EXAMPLES

Synthesis of the phenylglycine modified GSH backbones, containing the reduced and the urethane peptide bond isosteres was performed in analogy with previously reported methods Burg, D. et al. (2002), *Bioorg. Med. Chem.* 10, 195–205. This document is incorporated herein be reference.

Fmoc-Cys(Acm)-OtBu was first condensed with H-Phg-OtBu to give 1 (Scheme 1). After removal of the Fmoc protecting group (→2) the amine was derivatized with an o-nitrobenzenesulfonyl group to make the amino proton sufficiently acidic for Mitsunobu transformation. NMR analysis indicated that racemization of the phenylglycine moiety had occurred, presumably during the base catalyzed Fmor-removal. Reaction of alcohol 4 with the oNs-protected dipeptide 3 under Mitsunobu conditions gave the desired reduced peptide isostere 5. The o-nitrobenzenesulfonyl protecting-group was removed with thiophenol/DiPEA (→6). The free amine was then Boc-protected (→7) to prevent possible side-reactions during further steps and to facilitate purification. The Acm group was removed with $I_2$ to yield the symmetrical disulfide. After reduction of the disulfide with tri-n-butylphosphine, the free sulfhydryl was conjugated to a series of electrophiles and bromides to yield compounds 9–14. Synthesis of the benzyl-coupled compound 13 can be significantly shortened by using S-benzyl-protected cysteine as building block. The acid labile Boc and tBu groups were removed with TFA, to yield I–VI (FIG. 1).

The urethane peptidomimetic VII was acylated to yield its nitro-phenylcarbonate (15), which was condensed with the amino group of H-Cys(Acm)-Phg-OtBu (2). The obtained urethane-based mimetic was then deprotected and the sulfhydryl was alkylated as described above. This method can be used to make a large series of thiol-derivatized urethane peptidomimetics, containing the phenylglycine moiety. Synthesis, of this benzyl-coupled compound can be significantly shortened by using S-benzyl-protected cysteine as building block.

Ethyl ester derivatives of compounds V and VII were prepared by reaction with thionyl-chloride in dry ethanol, LC-MS analysis indicated that the main products were di-ethyl ester derivatives. All final compounds and their ethyl esters were purified on LH20 columns and by semi-preparative HPLC.

Materials: Protected amino acids were obtained from Bachem (Bubensdorf, Switzerland). Aromatic bromides were from Fluka Chemie (Buchs, Switzerland). Ethacrynic acid was from Sigma (St. Louis, Mo., USA). All solvents were of analytical grade and were dried and stored on molecular sieves when necessary. Recombinant human GST isoenzymes A1-1, M1-1 and P1-1 were purchased from PanVers Corporation (Madison, Wis., USA). GST assays were performed in 96 well plates using a Perkin Elmer HTS7000 BioAssay Reader. Cell-culture media and additives were from Life Technologies.

Synthesis: $^1$H and $^{13}$C-NMR spectra were recorded on Bruker AC-200, Bruker WM-300 or Bruker DMX-600 spectrometers, operating at 200/50.1, 300/75 and 600/150 MHz respectively. Chemical shifts are given in ppm ($\delta$) relative to the internal standard tetramethylsilane. Mass spectra were recorded with Finnigan MAT TSQ70 triple quadrupole, or with Perkin Elmer Sciex API 165 mass spectrometers. HPLC purification was performed on a Kratos spectroflow 400 system equipped with a Supelcosil SPLC-18-DB semi-preparative column. A linear gradient of 5–50% acetonitrile in $H_2O$/0.1%TFA was used to purify end products.

Fmoc-Cys(Acm)-Phg-OtBu (1)

To a solution of Fmoc-Cys(Acm)-OH (855 mg, 2 mmol) in 4 ml dry DCM at 0° C., HOBt (270 mg, 2 mmol) was added. Then an ice-cold solution of H-Phg-OtBu (415 mg, 2 mmol) in 4 ml of dry DCM was added. Subsequently, DIC (319 µl, 2 mmol) was introduced dropwise. After 1 h at 0° C. and 4 h at 4° C., the solution was evaporated under vacuum. The residue was dissolved in 50 ml EtOAc and washed with sat. aq. $NaHCO_3$, 0.5 M HCl and water. After drying and evaporation of the organic phase, the residue was chromatographed on silica gel to give the protected dipeptide 1 as a foam. Yield 1.14 g (95%), $R_f$ 0.35 (DCM/MeOH, 95:5). $^1$H NMR (CDCL$_3$): $\delta$1.45 (9H, s, tBu), 1.92 (3H, s, $CH_3$ Acm), 2.71–3.1 (2H, m, $C_\beta H_2$ Cys), 3.8 (1H, m, $C_\alpha$H Cys) 4.2–4.5 (5H,m, $CH_2$ Acm. CH—$CH_2$ Fmoc), 4.56–4.85 (3H, m, $C_\alpha$H Phg, Fmoc), 5.4 (1H, d, J=7.3 Hz, NH) 6.47 (1H, d, J=8.4 Hz, NH), 7.2–8.05 (14H, Fmoc+Phg aromatic, NH Acm). $^{13}$C NMR (CDCl$_3$): $\delta$23.7 ($CH_2$, Acm), 27.7 (3×$CH_3$, tBu), 34.9 ($C_\beta$, Cys), 41.1 ($CH_2$, Acm), 41.9 ($CH_2$, Fmoc), 57.4 ($C_\alpha$Phg), 83.7 ($C_q$ tBu), 119.7–127.5 (aromatic, Fmoc, Phg), 141.0 and 143.6 (4C, Fmoc), 156.6 (CO, Fmoc), 170.2 (CO, Cys), 173.5 (2×CO, Acm, tBu ester).

H-Cys(Acm)-Phg-OtBu (2)

1 (905 mg, 1.5 mmol) was dissolved in 5 ml dry DCM. DBU (224 mg, 1.5 mmol) was added at room temperature. After 15 min at room temperature, the solution was evaporated under reduced pressure. The crude product was used without further purification. $R_f$ 0.2 (DCM/MeOH, 9:1).

oNs-Cys(Acm)-Phg-OtBu (3)

The crude Fmoc deprotected dipeptide 2 (760 mg, 2 mmol) was dissolved in 10 ml dry DCM. The solution was cooled on an ice/water bath, after which DiPEA (380 mg, 2.2 mmol) and 2-nitrobenzenesulfonylchloride (488 mg, 2.2 mmol) were added. After 16 hours at ambient temperature, the solvent was evaporated and product 3 was purified by silica gel column chromatography. Yield 802 mg (75% over two steps). $R_f$ 0.35 (DCM/MeOH, 95:5). $^1$H NMR (CDCl$_3$): $\delta$1.45 (9H, s, tBu), 1.91 (3H, s, $CH_3$ Acm), 2.6–3.0 (2H, m, $C_\beta H_2$ Cys), 3.95–4.15 (2H, m, $CH_2$ Acm), 4.12 (1H, $C_\alpha$H Cys), 4.5 (3H, m, $C_\alpha$H Phg+$CH_2$ Acm), 5.2 (1H, d, J=7.3Hz), 6.95 (1H, m, NH), 7.2–8.2 (10H, m, aromatic oNs Phg, NH Acm). $^{13}$C NMR (CDCl$_3$): $\delta$23.7 ($CH_3$ Acm), 28.7 (3×$CH_3$ tBu), 34.9 ($C_\beta$ Cys), 41.1 ($CH_2$ Acm), 57.4 ($C_\alpha$Phg), 58.4 ($C_\alpha$ Cys), 83.7 ($C_\alpha$ tBu), 126.5–127.5 (aromatic oNs+Phg), 134.5 and 137.5 (aromatic), 148.6 (CO), 170.2 (CO Cys), 173.5 (2×CO Acm+tBu ester).

Boc-Glutaminol-OtBu (4)

Boc-Glu-OtBu (456 mg, 1.5 mmol) was dissolved in 5 ml freshly distilled THF and cooled to −40° C. under a stream of $N_2$ gas. Triethylamine (251 µL, 1.8 mmol) was added to the cold solution, followed by dropwise addition of isobutylchloroformate (236 µL, 1.8 mmol) in 1 ml THF. The resulting suspension was stirred at −20° C. for 45 minutes. The suspension was then filtered into a rigorously stirred solution of $NaBh_4$ in 2 ml $THF/H_2O$ (8/1) at 0° C. the reduction was then allowed to stir for 3 hours at RT. The solvent was then removed under reduced pressure and compound 4 was purified by silica gel column chromatography, using EtOAc/hexanes (1/1) as eluent. Yield 386 mg (89%). $R_f$ 0.45 (DCM/MeOH, 95:5). $^1$H NMR (CDCl$_3$): $\delta$1.45 (18H, 2×s, Boc, tBu), 1.54–1.95 (4H, m, $C_\beta H_2$, $C_\gamma H_2$), 3.65 (2H, t, J=5.9Hz, $C_\delta H_2$), 4.16 (1H, m, $C_\alpha$H), 5.34 (1H, d, J=8.4Hz, NH).

Boc-glu[Ψ($CH_2$N-oNS)-Cys(Acm)-Phg-OtBu]-OtBu (5)

To a stirred solution of triphenylphosphine (394 mg, 1.5 mmol) in 15 ml freshly distilled THF, DIAD (291 µL, 1.5 mmol) was added at −50° C. in an argon atmosphere. After 15 minutes, a white suspension had formed, to which a solution of alcohol 4 (288 mg, 1 mmol) and oNs-protected dipeptide 3 (534 mg, 1 mmol) in 7 ml THF was added dropwise. The temperature was carefully maintained at −50° C. during the peptide/alcohol addition. Afterwards, the reaction mixture slowly allowed to reach room temperature and was stirred overnight. The solvent was removed and product 5 was purified over a silica gel column. The product was collected as an oil. Yield 650 mg (80%). $R_f$ 0.35 (DCM/MeOH, 9:1). $^1$H NMR (CDCl$_3$): $\delta$1.45 (27H, s, Boc, tBu), 1.5–1.85 (2H, m, $C_\beta H_2$ Glu), 1.9 (3H, s, $CH_3$ Acm), 2.73–3.25 (2H, m, $C_\beta H_2$ Cys), 3.46 (2H, m, $C_\gamma H_2$ Glu), 3.95–4.1 (2H, m, $CH_2$ Acm), 4.35–4.7 (2H, m $C_\alpha$H Phg+$C_\alpha$H Glu), 4.9 (1H, m $C_\alpha$H Cys), 5.35 (1H, d J=7.2Hz, NH), 7.3–8.15 (10H, NH, aromatic oNa+Phg). $^{13}$C NMR (CDCl$_3$): $\delta$21.9 ($CH_3$ Acm), 26.3 $C_\gamma$ Glu), 27.8–28.15 (Boc, tBu), 28.9 ($C_\beta$ Glu), 30.6 ($C_\beta$ Cys), 40.0 ($CH_2$ Acm), 45.2 ($C_\beta$ Glu), 53.4 ($C_\alpha$ Glu), 56.9 ($C_\alpha$ Phg), 58.6 ($C_\alpha$ Cys), 79.2, 81.4, 81.1 ($C_q$ Boc, tBu), 123.7–136.0 (9C, aromatic), 147.9 (C=$NO_2$), 155.7 (CO Boc), 168.2–171.59 (4×CO).

Boc-Glu[Ψ($CH_2$NH)-Cys(Acm)-Phg-OtBu]-OtBu (6)

Compound 5 (584 mg, 0.8 mmol) was dissolved in 15 ml dry DMF in an $N_2$-atmosphere. Thiophenol (409 µL, 4 mmol) and DiPEA (552 µL, 3.2 mmol) were added, after which the mixture was stirred overnight. Toluene was added to the reaction mixture and applied to a silica gel column. Flushing with toluene was continued until excess thiophenol and brightly coloured deprotection by-products had eluted.

The eluent was then replaced by EtOAc/hexanes, after which product 6 could be isolated as an oil. Yield 436 mg (88%). $R_f$ 0.15 (DCM/MeOH, 95:5). $^1$H NMR (CDCL$_3$): δ1.41 (27H, ss, Boc, tBu), 1.54 (2H, m, $C_\gamma H_2$ Glu), 1.74 (2H, m $C_\beta H_2$ Glu), 1.98 (3H, s, CH$_3$ Acm), 2.52–3.05 (2H, $C_\beta H_2$ Cys), 2.93 (2H, m, $C_\delta H_2$ Glu), 3.3 (1H, m, $C_\alpha H$ Cys), 4.18–4.3 (4H, m, $C_\alpha H$ Glu+CH$_2$ Acm+$C_\alpha H$ Phg), 5.35 (1H, d, J=8.4Hz, NH Boc), 7.0 (1H, m, NH Acm), 7.3 (5H, m, arom Phg), 8.3 (1H, m, NH Phg), $^{13}$C NMR (CDCl$_3$): δ22.3 (CH$_3$ Acm), 25.3 ($C_\gamma$ Glu), 27.5–28.0 (Boc, tBu), 29.5 ($C_\beta$ Glu), 33.2 ($C_\beta$ Cys), 41.0 (CH$_2$ Acm), 47.5 ($C_\beta$ Glu), 54.0 ($C_\alpha$ Glu), 56.8 ($C_\alpha$ Phg), 61.0 ($C_\alpha$ Cys), 77.6–82.0 (3×$C_q$, Boc, tBu), 126.8–128.3 (CH aromatic), 137.1 (C aromatic) 155.1 (CO Boc), 169.0–171.4 (4×CO).

Boc-Glu[Ψ(CH$_2$N-Boc)-Cys(Acm)-Phg-OtBu]-OtBu (7)

Reduced peptide isostere 6 (434 mg, 0.7 mmol) was dissolved in 20 ml dry acetonitrile. DiPEA (0.155 μL, 0.9 mmol) and BOC$_2$O (350 mg, 1.6 mmol) were added. The mixture was stirred at 80° C. for 24 hours, until no starting material could be detected by TLC. EtOAc (100 ml) was added and the organic phase was washed with sat aq. NaHCO$_3$, 0.1 M HCl and water. The organic solvent was evaporated under reduced pressure. Compound 7 was obtained as an oil after silica gel column chromatography, using BtOAc/hexanes as eluent. Yield 363 mg (72%). $R_f$ 0.3 (DCM/MeOH, 95:5). $^1$H NMR (CDCl$_3$): δ1.45 (36H, ss, Boc, tBu), 1.5–1.8 (4H, m, $C_\beta H_2$ Glu, $C_\alpha H_2$ Glu), 2.01 (3H, s, CH$_3$ Acm), 2.85 and 3.2 (2H, m, $C_\beta H_2$ Cys), 3.17 (2H, m $C_\delta H_2$ Glu), 3.9 (2H, m, CH$_2$ Gly), 4.23 (1H, m $C_\alpha H$ Glu), 4.54 (2H, m, CH$_2$ Acm), 4.67 (1H, m, $C_\alpha H$ Cys), 5.18 (1H, d, J=8.0Hz) 6.9 (2H, m, NH Acm NHGly). $^{13}$C NMR (CDCl$_3$/MeOD): δ22.6 (CH$_3$ Acm), 25.0 ($C_\gamma$ Glu), 27.6–28.0 (Boc, tBu), 29.2 ($C_\beta$ Glu), 30.3 ($C_\beta$ Glu), 41.0 (CH$_2$ Acm), 45.1 ($C_\delta$ Glu), 53.5 ($C_\alpha$ Glu), 56.8 ($C_\alpha$ Phg+$C_\alpha$ Cys), 7.6–82.0 (4× $C_q$, Boc, tBu), 126.7–128.3 (CH aromatic), 136.5 (C aromatic) 155.1–156.03 (2× CO Boc), 169.0–171.4 (4× CO).

(Boc-Glu[Ψ(CH$_2$N-Boc)-Cys-Phg-OtBu]-OtBu)$_2$ (8)

Peptide 7 (362 mg, 0.5 mmol) was dissolved in 10 ml dry MeOH. A solution of I$_2$ (254 mg, 1 mmol) in 5 ml MeOH was added dropwise over 30 min. After 10 min TLC analysis indicated complete disulfide formation. The solution was then decolorized by addition of 1 M sodium thiosulfate solution. EtOAc (100 ml) was added and the organic phase was washed with thiosulate solution and water. Solvents were then evaporated in vacuo and product 8 was purified on a Sephadex LH20 column, using DCM/MeOH (1:1) as eluent. Yield 93%, $R_f$ 0.45 (DCM/MeOH, 95/5). $^1$H NMR (CDCL$_3$); δ1.45 (72H, s, Boc, tBu), 1.5–1.82 (8H, m, $C_\beta H_2$ Glu, $C_\gamma H_2$ Glu), 2.8–3.6 (8H, m, $C_\delta H_2$ Glu, $C_\beta H_2$ Cys), 4.12 (2H, m, $C_\alpha H$ Glu) 4.9 (2H, m, $C_\alpha H$ Cys) 5.15 (2H, d, NH Boc) 7.45 (2H, m, NH Gly).

Boc-Glu[Ψ(CH$_2$N-Boc)-Cys(R)-Phg-OtBu]-OtBu (9–14)

The protected disulfide 8 (0.1 mmol) was dissolved in 5 ml nPrOH/H$_2$O (4/1). The pH was adjusted to 8.5 with 25% aq NH$_4$OH solution and the mixture was flushed with argon. After addition of tri-n-butylphosphine (25 μL, 0.1 mmol), the resulting mixture was stirred for 1 h at room temperature. Ethacrynic acid (→9) p-methoxyphenacylbromide (→10), phenacylbromide (→11), 4-vinylpyidine (→12), benzylbromide (→13) or 2-bromoheptane (→14) (1 mmol) dissolved in 1 ml EtOH was added. After 24 hr at RT, the solvent was evaporated. The residue was purified by silica gel column chromatography, using DCM/MeOH (95/5) as eluent. The protected EA-conjugate was collected as an oil. Yield 65–80%, dependent on which substrate was used, NMR data corresponded with the appropriate thiol modified, fully protected tripeptides.

H-Glu[Ψ(CH$_2$NH)-Cys(R)-Phg-OtBu]-OH, I–VI (in table 2)

Deprotection of 9–14 was performed by addition of 5 ml TFA/H$_2$O (99/1). After 4 h at RT, the product was precipitated by addition of ice-cold diethylether. Further purification of the precipitate by Sephadex LH20 column chromatography, eluent: MeOH/H$_2$O (7/3), yielded compounds I–V. The pure reduced tripeptide-conjugates was obtained after HPLC purification. LC-MS analysis confirmed the presence of the indicated products.

Boc-Glo(ONp)-OtBu (15)

Boc-Ser(OtBu) (261.2 mg, 1.5 mmol) was dissolved in 20 ml DMF. Bis(4-nitrophenyl)carbonate (456 mg, 1.5 mmol) and DiPEA (259 μL, 1.5 mmol) were added, after which the resulting solution was stirred for 16 hours at room temperature. EtOAc (100 ml) was added to the mixture, which was then repeatedly washed with saturated NaHCO$_3$ until the aqueous layer was no longer yellow. After drying and evaporation of the organic layer, the product was purified by silica gel column chromatography. The carbonate 15 was collected as a foam. Yield 582 mg (91%), $R_f$0.85 (DCM/MeOH, 95:5). $^1$H NMR (CDCl$_3$): δ 1.4 (9H, s, Boc), 1.5 (9H, s, tBu), 4.61 (3H, m, $C_\alpha H$, $C_\beta H_2$), 5.62 (1H, d, J=6.5Hz, NH), 7.4 (2H, aromatic) and 8.25 (2H aromatic).

Boc-Glo[Cys(Acm)-Phg-OtBu]-OtBu (16)

A solution of 2 (572 mg, 1.5 mmol) in 2.5 ml dioxane was added to a solution of 15 (582 mg, 1.35 mmol) in 2.5 ml dioxane. The mixture was stirred at 80° C. overnight. After evaporation of the solvent, the residue was dissolved in 50 ml EtOAc. Washing with saturated aq. Na$_2$CO$_3$ was repeated until the aqueous layer was colorless. Silica gel column chromatography gave the pure tripeptide 16 as a foam. Yield 622 mg (78%). $R_f$ 0.48 (DCM/MeOH, 9:1). $^1$H NMR (CDCl$_3$); δ1.45 (27H, s, Boc+tBu), 2.0 (3H, s, Ch$_3$ Acm), 2.8–3.0 (2H, m, $C_\beta H_2$ Cys), 3.8–4.1 (2H, m, CH$_2$ Acm), 4.1–4.6 (5H, m, $C_\alpha H$ Cys $C_\alpha H$, $C_\alpha H$ Phg, $C_\beta H_2$Glo), 5.6 (1H, d, NH Boc), 6.2 (1H, d, NH Glo), 7.3 (2H, 2×NH, Acm and Phg amide). $^{13}$C NMR (CDCl$_3$): δ22.8 (CH$_3$ ACM), 27.4–28.0 (9×CH$_3$, Boc, tBu), 33.7 ($C_\beta$ Cys), 40.4 (CH$_2$ Acm), 53.2 (Cα Phg), 54.7 ($C_\alpha$ Cys, $C_\alpha$ Glo), 65 ($C_\beta$ Glo), 79.5–82.2 (3×$C_{quart}$, Boc, tBu), 155.1 (CO, Boc), 155.8 (CO, Glo), 168.4–171.3 (4×CO).

(Boc-Glo[Cys-Phg-OtBu]-OtBu)$_2$ (17)

Compound 16 (591 mg, 0.5 mmol) was dissolved in 7 ml of dry MeOH. A solution of I$_2$ (254 mg, 1 mmol) in 3 ml MeOH was added dropwise during 30 minutes. After 10 min. at room temperature, the mixture was cooled to 0° C. and decolorized with 1 M aq. Na$_2$S$_2$O$_3$ solution. The resulting mixture was diluted with 100 ml EtOAc and washed with 1 M aq. Na$_2$S$_2$O$_3$ solution and water. After drying and evaporation of the organic phase, the residue was dissolved in DCM/MeOH (1/1) and purified by Sephadex LH20 gelfiltration chromatography, using DCM/MeOH as eluent. The pure disulfide 17 was obtained as a white foam. Yield 288 mg (95%). $R_f$ 0.41 (DCM/MeOH, 9:1). $^1$H NMR (CDCl$_3$): δ1.45 (54H, s, Boc, tBu), 2.95 (4H, m, $C_\beta H_2$), 4.3–4.5 (8H, $C_\alpha H$ Glo, $C_\alpha H$ Phg, $C_\beta H_2$ Glo), 4.98 (2H, m, $C_\alpha H$ Cys), 5.4 (2H, d, J=8Hz, NH Boc), 5.9 (2H, d, J=8.2Hz, NH Glo), 7.8 (2H, m, NH)

(H-Glo[Cys-Phg-OH]-OH)$_2$ (18)

Disulfide 17 (288 mg, 0.24 mmol) was dissolved in 5 ml TFA/100 μLH$_2$O. After 3 hours at RT, the deprotected peptide was precipitated by addition of 15 ml ice-cold diethylether. The disulfide (TFA salt) 18 was used without further purification.

H-Glo[Cys(Bzl)-Phg-OH]-OH (VII)

The deprotected disulphide 18 (144 mg, 0.12 mmol) was dissolved in 5 ml nPrOH/H$_2$O (3:1). Aqueous ammonia solution (25%) was added until pH 8.5. After flushing with N$_2$, tri-n-butylphosphine (31 μL, 0.13 mmol) was added and the solution was stirred for 60 minutes at room temperature. A solution of benzylbromide (171 mg, 1 mmol) in 5 ml nPrOH was added. After adjusting the solution to pH 8 with 1 M NaOH, stirring was maintained for 4 hours. The solvent was evaporated under reduced pressure, after which the residue was dissolved in water. The aqueous solution was extracted with EtOAc and purified by Sephadex LH20 column chromatography, using MeOH/H$_2$O (7/3) as eluent. Product VII was further purified by reversed phase HPLC to yield a fluffy white powder after lyophilization. R$_f$ 0.35 (nBuOH/H$_2$O/AcOH, 15:3:2). Mass spectrometry (ES-MS) m/e: 474.5 [M-H]$^-$ (Negative mode)

Evaluation of metabolically stabilized GST P1-1 inhibitors.

I: GluPhg-Benzyl

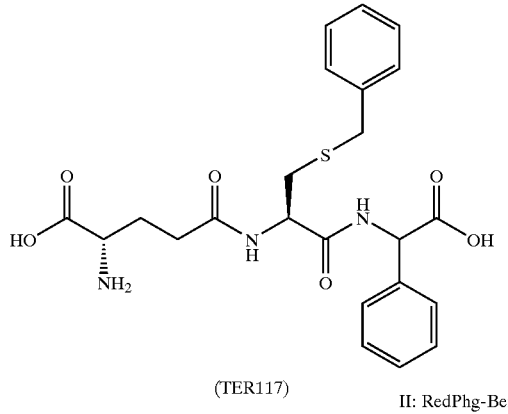

(TER117)

II: RedPhg-Benzyl

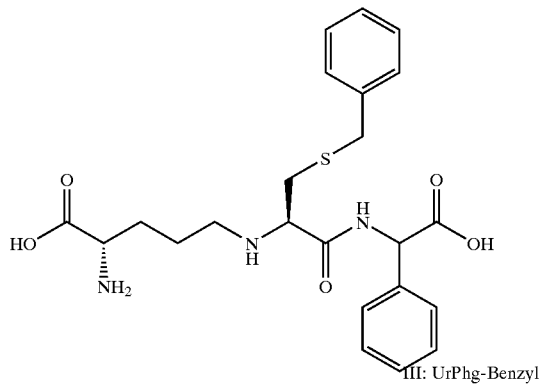

III: UrPhg-Benzyl

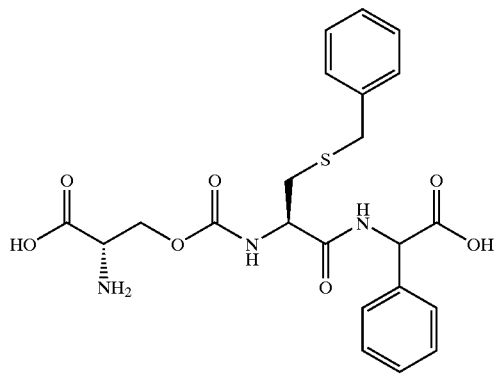

GluPhg-Benzyl (structure I above; γ-L-glutamyl-L-cysteinyl(benzyl)-D-phenylglycine, also known as TER117) contains a γ-glutamyl transpeptidase sensitive γ-glue-cys peptide bond, which is responsible for its rapid breakdown in vivo. This peptide-bond was stabilized towards γGT by introduction of a peptidomimetic "reduced" amide (structure II, RedPhg-Benzyl), or by introduction of a urethane isostere (structure III, UrPhg-Benzyl). Selection of the benzyl group on the cystein S is based on the results presented in table 2.

The new peptidase stabilized structures are selective potent inhibitors of GST P1-1, see table 1. RedPhg-Beznyl and UrPhg-Benzyl contain both D- and L-phenylglycine, of which the D-diastereomer is the active GST P1-1 inhibitor. This may therefore be the reason for the slightly reduced inhibitory potency compared to GluPhg-Benzyl. It is expected inhibitory potency will be improved when diastereomerically pure compounds are used.

TABLE 1

K$_i$ values determined for inhibition of human GST isoenzymes by the GST inhibitors

| Inhibitor | GSTA1-1 | GSTM1-1 K$_i$ values (μM ± SD) | GSTP1-1 |
|---|---|---|---|
| GluPhg-Benzyl (I) | 23 ± 6 | 21 ± 4 | 0.8 ± 0.3 |
| RedPhg-Benzyl (II) | 55 ± 11 | 29 ± 6 | 6 ± 3 |
| UrPhg-Benzyl (III) | 29 ± 4 | 16 ± 2 | 3 ± 2 |

Cell-membrane permeable diethyl ester derivatives of GluPhg-Benzyl (the diethylester of TER117 is known as TER199), RedPhg-Benzyl (compound Vb in FIG. 1) and UrPhg-Benzyl (compound VIIb in FIG. 2) were prepared and evaluated for this activity in the mammary carcinoma cell lines MTLn3 (and its GST P1-1 transfected derivative) and MCF7 (and its multidrug-resistant derivative VCREMS). The new inhibitors were shown to partially reverse drug resistance of these cells towards the alkylating cytostatic thiotepa, see table 3.

Stability towards γ-Glutamyl transpeptidase (γGT).

The rate of degradation was determined by incubating 250 μM of GluPhg-Benzyl, RedPhg-Benzyl and UtPhg-Benzyl at 37° C. with 0.25 mg/ml bovine kidney γ-glutamyl transpeptidase in 0.1 M Tri-HCl buffer, pH 7.4, supplemented with 0.1 mM EDTA. At selected time-intervals, a 100 μL sample was taken, heat-inactivated, and stored on ice until HPLC-analysis. Analysis was performed by RP-HPLC on an Altech Platinum C18 column, using 50 mM ammonium acetate buffer pH 3.8, supplemented with 10–20% acetonitrile (optimized for the various peptide analogues) as eluent. Disappearance of the parent peak was determined by UV absorbency at 254 mm. Remaining percentage of the parent compounds was determined as ratio of peak areas relative to the initial (t=0min) value.

TABLE 2

Structures of the GST inhibitors and their inhibition of GSTP1-1. *marks the position of attachment to the sulfhydryl group of backbone A or B. Inhibition was tested using 1 mM GSH and 1 mM CDNB in the presence of 50 μM inhibitor. Inhibition is shown as percentage inhibition with respect to the non-inhibited reaction rate, corrected for the non-enzymatic reaction rate.

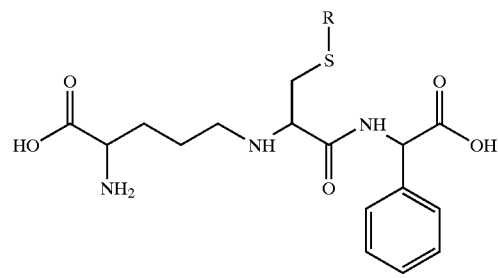

A

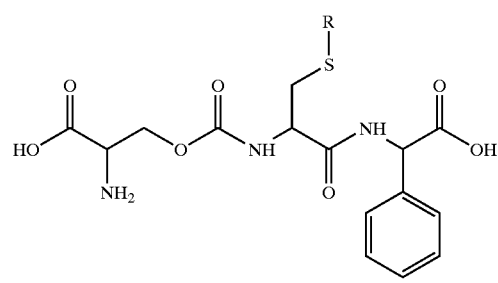

B

| compound | peptide backbone | R | % inhibition of GSTP1-1 [inhibitor] = 50 μm |
|---|---|---|---|
| I: RP-EA | A | ![](Cl, Cl, OH substituted aryl ketone with ethyl branch) | 100 |
| I: RP-MPA | A | ![](4-methoxyphenyl ketone) | 92 |
| III: RP-PA | A | ![](phenyl ketone) | 58 |
| IV: RP-VP | A | | 43 |
| V: RP-Bzl | A | | 81 |
| VI RP-sHep | A | | 39 |
| VII: UP-Bzl | B | | 93 |

GST inhibition experiments.

Human recombinant GST isoenzymes A1-1, M1-1 and P1-1 were used for the GST inhibition assays. Experiments were performed according to Habig et al; (1974), *J. Biol. Chem.* 249, 7130–7139, modified for a 96-wells plate-reader assay. The purified human GST isoenzymes (10–20 ng/ml) were incubated with or without inhibitor (50 μM) in the presence of 8 different concentrations (50 μM–4 mM) GSH at 37° C. in 0.1 M potassium phosphate buffer pH 6.5/1 mM EDTA. The reaction was initiated by addition of CDNB in ethanol (final concentration 1 mM, 1% ethanol in assay mix), after which the formation of GS-DNB was spectrophotometrically monitored at 340 nm. Reaction rates were corrected for the non-enzymatic conjugate formation. $K_i$ values (table 1) were determined using the $K_{m,\ app}$ method according to Kakkar et al. (1999), *Drug Metab. Dispos.* 27, 756–762; Kakkar et al. (2000), *J. Pharmacol. Exp. Ther.* 293, 861–869. Experiments were performed three times with quadruple measurements.

Modulation of resistance of cancer cell lines toward Thiotepa.

Cells (MCF7, VCREMS, 3 MTLn3/neo clones and 3 MTLn3/GSTP1-1 clones) were seeded at $10^4$ cells/well in 24-wells polyethylene culture dishes. After overnight attachment, culture medium was replaced by Hanks' Balanced Salt solution, containing the GST inhibitor (25 μM). Various concentrations (3 μM-10 mM) of thiotepa (in serum-free medium) were added. After 4 hrs at 37° C., cells were washed twice with PBS, and subsequently incubated for 72 hours in culture medium (in absence of inhibitor). The cells were then rinsed once with BPS and lysed by repeated freeze-thaw cycles in 200 μl water, followed by homogenization on a rotary shaker. Cell proliferation was measured by DNA content, using Hoechst-33258 staining. In short: 50 μl Hoechst 33258 (20 μg/ml in TNE; 10 mM Tris, 1 mM EDTA, 0.2 M NaCl, pH 7.4) was added to 50 μl lysate. Stained DNA was measured by spectrofluorometry (excitation: 360 nm, emission 465 nm). A calibration curve of calf thymus DNA was used to determine total DNA quantities. Growth curves were calculated using the $IC_{50}$ module of the enzyme kinetics program Grafit (version 3.0, Erithacus Software Ltd.).

TABLE 3

Modulation of thiotepa cytotoxicity by the GSTP1-1 inhibitors.

| | $IC_{50}$ value in μM | | | |
|---|---|---|---|---|
| Cell line | No Inh | GluPhg-Benzyl | RedPhg-Benzyl | UrPhg-Benzyl |
| MTLn3/Neo | 164 ± 9 | 113 ± 11 | 109 ± 53 | 129 ± 16 |
| MTLn3/GSTπ | 219 ± 21 | 137 ± 8 | 119 ± 12 | 121 ± 12 |
| MCF7 | 699 ± 50 | 446 ± 34 | 314 ± 35 | 324 ± 33 |
| VCREMS | 2840 ± 1100 | 315 ± 40 | 340 ± 68 | 200 ± 92 |

GST Pi oligomerization and JNK activation.

Confluent monolayers of VCREMS, MTLn3/Neo (3 clones) and MTLn3/GSTπ (3 clones) cells in 12-well culture dishes were exposed for 8 or 16 hours to 50 μM of Et$_2$-RP-Bzl, Et$_2$-UrP-Bzl or 20 μM TER199 (all di-ethyl esters) in full medium at 37° C. Cells were then washed and subsequently scraped in ice-cold PBS. For MTLn3 cells, suspensions of the three different neo and three different GSTπ clones were combined. After centrifugation (10 min, 250 g, 4° C.), the cells were lysed by ultrasonication in cold TSB (10 mM Tris, 250 mM sucrose, 1 mM EGTA, pH 7.4), containing protease inhibitors (50 mM Na$_3$VO$_4$, 10 μg/ml leupeptin, 10 μg/ml pepstain, 1 mM phenylmethylsulfonylfuloride). Protein concentration was determined using the Bradford protein assay, using IgG as a standard.

Immunoblotting

For GSTπ blotting, non-reducing and non-denaturing conditions were used to keep GSTP in its original (homodimer) state. JNK blots were subjected to standard Western blotting sample pre-treatment protocols. Twenty micrograms of total cellular protein was separated by SDS-polyacrylamide gel electrophoresis and subsequently transferred to polyvinylidene difluoride membrane (Millipore). Blots were blocked with 5% (w/v) non-fat milk TBS-T (0.5 M NaCl, 20 mM Tris-HCl, 0.05% v/v Tween 20; pH 7.4) and probed for GSTπ (rabbit polyclonal) or phospho-JNK (rabbit polyclonal, Promega). A horseradish-peroxidase coupled goat anti rabbit antibody was used for detection of GSTπ, which was visualized with ECL reagent (Amersham Pharmacia Biotech). Active JNK was detected by an alkaline phosphatase coupled goat antibody, which was visualized with the Tropix kit (PerkinElmer Life Sciences).

The potent GSTP1-1 inhibitor TER 199 has been shown to induce GSTP oligomerization and JNK activation in various cell lines Adler, V, et al. (1999), *EMBO J.* 18, 1321–1334. GSTP is predominantly present in cells as non-covalently linked homodimers (GSTP1-1); the 46 kDa dimer was therefore the main band in all three cell lines. This band also includes GSTP-GSTP dimers eventually formed by intersubunit disulfide bonding of GSTP monomers. MTLn3 cells also show the monomeric GSTP subunit (Mw 23kD), a band that is not seen in VCREMS cells. Also bands at ≈21.5 and ≈37 kDa were detected, presumably corresponding to post-translationally modified GSTP. After 8 hours of exposure, an approximately 92 kDa band appears in MTLn3 cells, comprised of four GSTP subunits. This band was already present in non-treated (t=0) VCREMS cells. Larger aggregates are also formed as shown by small bands at higher molecular weights. Although the inhibitors had a clear effect on GSTP oligomerization in MTLn3 cells, no clear effects were observed in VCREMS cells. The response to GSTP1-1 inhibition is the most apparent at t=8 hours. After 16 hours, GSTP tetramer staining is less pronounced; after 24 hours of exposure, no GSTP oligomerization was seen. The novel inhibitors Et$_2$-RP-Bzl and Et$_2$-UrP-Bzl had the same effect on GSTP oligomerization as TER199.

After exposure to the GSTP1-1 inhibitors, both phosphorylation of JNK1 (46 kda) and JNK2 (54 kDa) occurs. Phospho-JNK is virtually absent in untreated MTLn3 cells, but is clearly present after 8 hours exposure to all three inhibitors. Importantly, in both neo and GSTπ MTLn3 cells, JNK activation occurs simultaneous with GSTP oligomerization: levels of phosphor-JNK were decreased again after 16 hours of exposure. VCREMS cells already display active JNK in absence of the inhibitors. GSTP1-1 inhibition only slightly increased the phospho-JNK levels in these cells. A correlation between the emergence of phospho-JNK and the reduction of the 23 kDa monomers GSTπ-bond was also observed. The absence of the GSTP1-1 monomer in VCREMS cells may therefore also be linked to the constitutively phophorylated JNK. All three inhibitors had the same effect on active JNK1 and JNK2 formation. Interestingly, after 8 hours exposure to Et$_2$-UrP-Bzl and TER199, a small band appeared just below the 54 kDa active JNK2 band, that may represent post-translationally modified JNK2. Its function is currently not known, but may be physiologically relevant.

GSH backbones comprising a glycine instead of a phenylglycine residue (see table 4)

Figure 2:
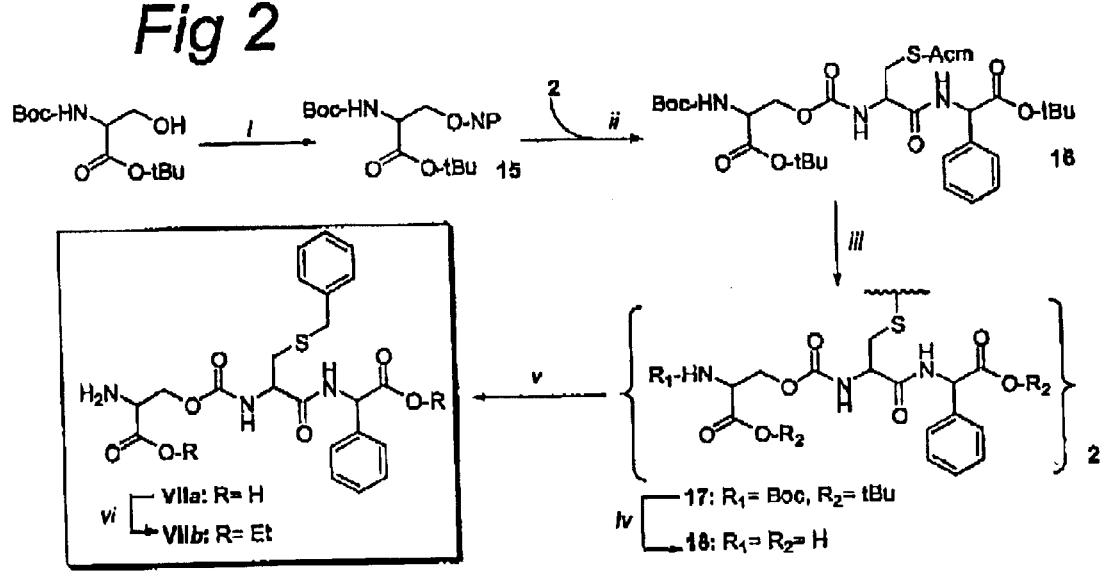
FIG. 2 (scheme 2) represents the synthesis of the urethane peptide isostere. Conditions: (i). Bis(4-nitrophenyl) carbonate, DiPEA, DMF; (ii). 2, dioxane, 80° C.; (iii), I$_2$, MeOH; (iv). TFA/H$_2$O (98:2, v/v); (v), tri-n-butylphosphine, nPrOH/H$_2$O (3:1, v/v), benzylbromide; (vi). SOCl$_2$, EtOH.
Figure 4:
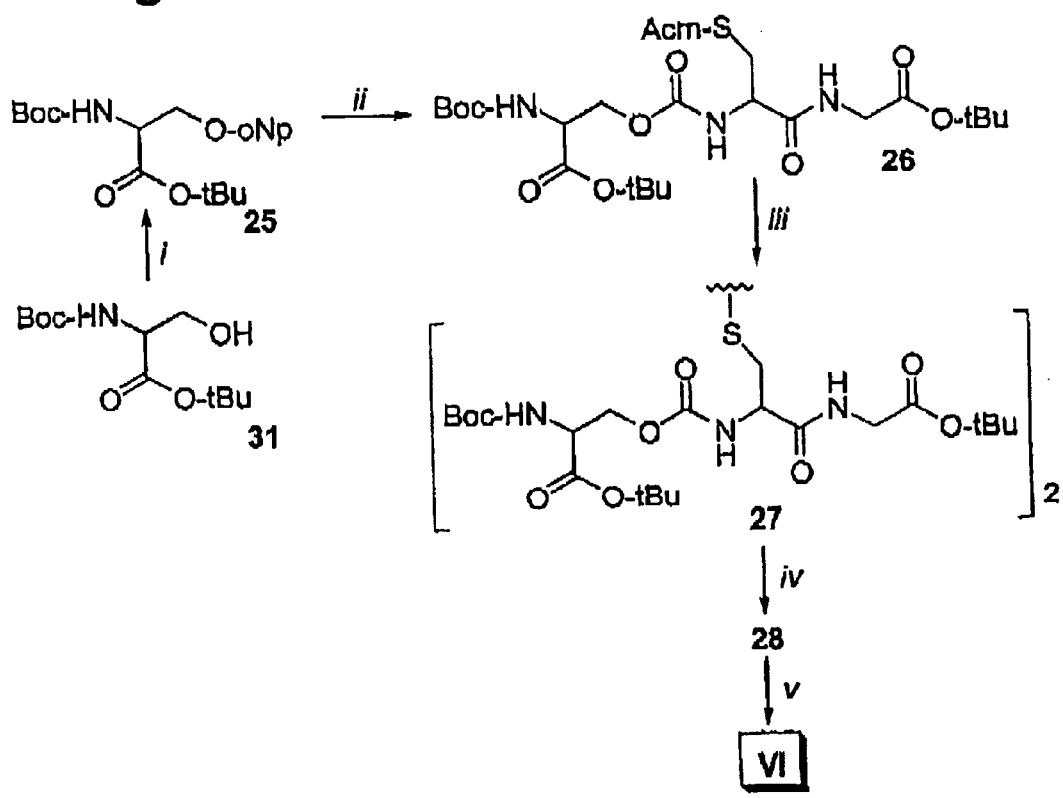
FIG. 4 (scheme 4) represents the urethane isostere synthesis. Conditions: i. 31, bis(4-nitrophenyl)carbonate, DiPEA, DMF. ii. 2 of FIG. 1 with a glycine group instead of a phenylglycine group, dioxane, 80° C. iii. I$_2$, MeOH. iv. TFA, 1%H$_2$O, v. Tri-n-butylphosphine, nPrOH/H$_2$O, ethacrynic acid.
Figure 3:
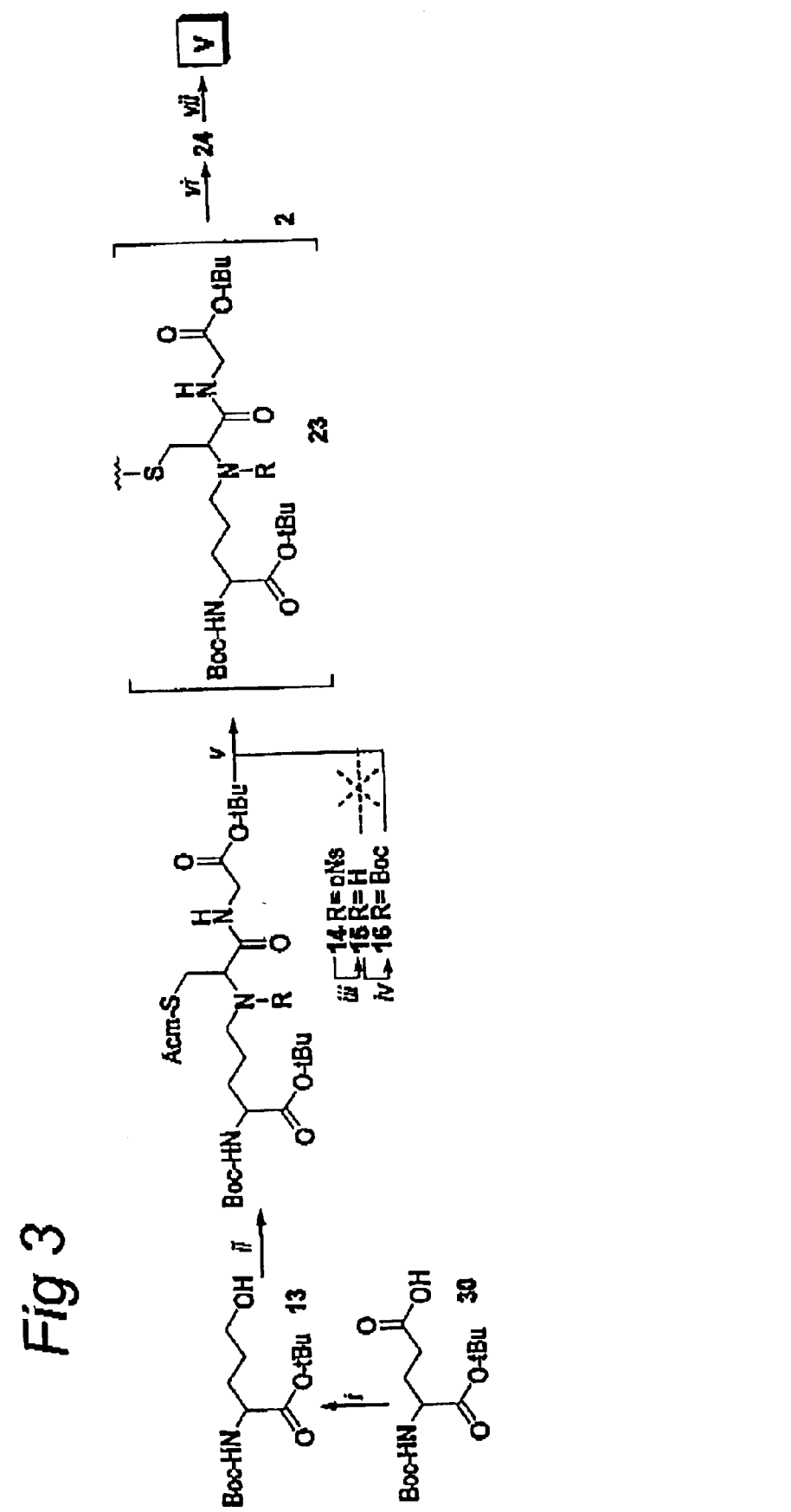
FIG. 3 (scheme 3) represents the preparation of the reduced isostere. Conditions: i. 30, isobutylchloroformate, triethylamine, NaBH$_4$, THF/H$_2$O. ii. Triphenylphosphine, DIAD, 3 of FIG. 1 with a glycine group instead of a phenylglycine group, THF, iii. Thiophenol, DiPEA, DMF, iv. Boc$_2$O, DiPEA, MeCN, v. I$_2$, MeOH. vi. TFA, 1%H$_2$O. vii. Tri-n-butylphosphine, nPrOH/H$_2$O, ethacrynic acid.

As already stated above, the synthesis of compounds I–VI, in particular of compounds V and VI, defined in Table 4 proceeded analogously to the synthesis of compounds V in FIG. 1 (scheme 1) and compound VII in FIG. 2 (scheme 2) and has been published, Burg. D. et al. (2002), *Bioorg. Med. Chem.* 10, 195–205. The preparation of compound V is depicted in FIG. 3 (scheme 3). The reaction sequence towards urethane VI is depicted in FIG. 4 (scheme 4).

buffer, pH=7.4, supplemented with 0.1mM EDTA. At selected time-intervals, a 100 μL sample was taken, heat-inactivated, and stored on ice until HPLC-analysis. Analysis was performed by RP-HPLC on an Alltech Platinum C18 column, using 50mM ammonium acetate buffer pH=3.8, supplemented with 10–20% acetonitrile (optimized for the various peptide analogues) as eluent. Disappearance of the present peak and emergence of the corresponding dipeptide-EA conjugate was detected by UV absorbency at 270 nm. Remaining percentage of the parent compounds was determined as ratio of peak areas relative to the initial (t=0 min)

TABLE 4

Structure of the Glutathione-ethacrynic acid conjugate (I) and peptidomimetic analogues.
I = γ-Glu[Cys(EA)-Gly-OH]—OH (GS-EA), II = γ-Glu[Cys(EA)-Src-OH]—OH,
III = γ-Glu[MeCys-Gly-OH]—OH, IV = γ-Glu[2-amino-1-mercapto(S-EA)-6-hexanoic acid]-OH, V = H-Glu[Ψ(CH$_2$NH)-Cys(EA)-Gly-OH]—OH, VI = H-Glo[Cys(EA)-Gly-OH]—OH

| | R1 | R2 | R3 | R4 | R5 |
|---|---|---|---|---|---|
| I | $CH_2$ | C=O | NH | C=O | NH |
| II | $CH_2$ | C=O | NH | C=O | N—$CH_3$ |
| III | $CH_2$ | C=O | N—$CH_3$ | C=O | NH |
| IV | $CH_2$ | C=O | NH | $CH_2$ | $CH_2$ |
| V | $CH_2$ | $CH_2$ | NH | C=O | NH |
| VI | O | C=O | NH | C=O | NH |

H-Glu[Ψ(CH$_2$NH)-Cys(EA)-Gly-OtBu]-OH, V

Purification by Sephadex LH20 column chromatography, eluent: MeOH/H$_2$O (7/3), yielded compound IV as a fluffy white powder after lyophilization. LC-MS analysis indicated the presence of the desired product and a tri-n-butylphosphine-EA complex. The pure reduced tripeptide-EA conjugate was obtained after HPLC purification. $R_f$ 0.3 (nBuOH/H$_2$O/AcOH, 15/3/2). $^1$H NMR (D$_2$O): δ0.86 (3H, t, CH$_3$EA), 1.55 (2H, m, CH$_2$EA), 1.74–1.92 (4H, m, C$_\beta$H$_2$, C$_\gamma$H$_2$) 2.4 (2H, m, C$_\delta$H$_2$) 2.85 (2H, dd, C$_\beta$H$_2$Cys), 3.0 (2H, m, CH$_2$EA), 3.74 (1H, d, C$_0$HEA) 3.78 (2H, d, CH$_2$Gly), 4.1 (1H, m, G$_\alpha$HGlu), 4.65 (2H, s, CH$_2$EA), 6.9, 7.6 (2×1H, dd, EA aromatic). Mass spectrometry (ES-MS): m/e: 596, [M+H]$^+$.

H-Glo[Cys(EA)-Gly-OH]-OH, VI

Purification by Sephadex LH20 column chromatography, using MeOH/H$_2$O (7/3) as eluent. Product VI was further purified by reversed phase HPLC to yield a fluffy white powder after lyophilization. $R_f$ 0.35 (nBuOH/H$_2$O/AcOH, 15/3/2). $^1$H NMR (D$_2$O): δ0.9 (3H, t, CH$_3$EA), 1.55 (2H, m, CH$_2$EA), 2.9 (2H, dd, C$_\beta$H$_2$Cys), 3.0 (2H, m, CH$_3$EA), 3.75 (1H, d, C$_\alpha$HEA) 3.9 (2H, d, CH$_2$Gly), 4.3–4.5 (3H, m, C$_\alpha$HGlo, C$_\beta$H$_2$Glo), 4.65 (2H, s, CH$_2$EA), 4.9 (2H, m, C$_\alpha$HCys), 6.9 and 7.6 (2× 1H, dd, EA aromatic). Mass spectrometry (ES-MS) m/e: 610, [M-H]$^-$ (Negative mode).

Stability towards γ-Glutamyl transpeptidase

The rate of degradation was determined by incubating 250 μM of the GS-EA analogues at 37° C. with 0.25 mg/ml bovine kidney γ-glutamyltranspeptidase in 0.1M Tris-HCl value. Results were corrected for non-peptidase mediated degradation of the ethacrynic acid conjugates.

Figure 5:
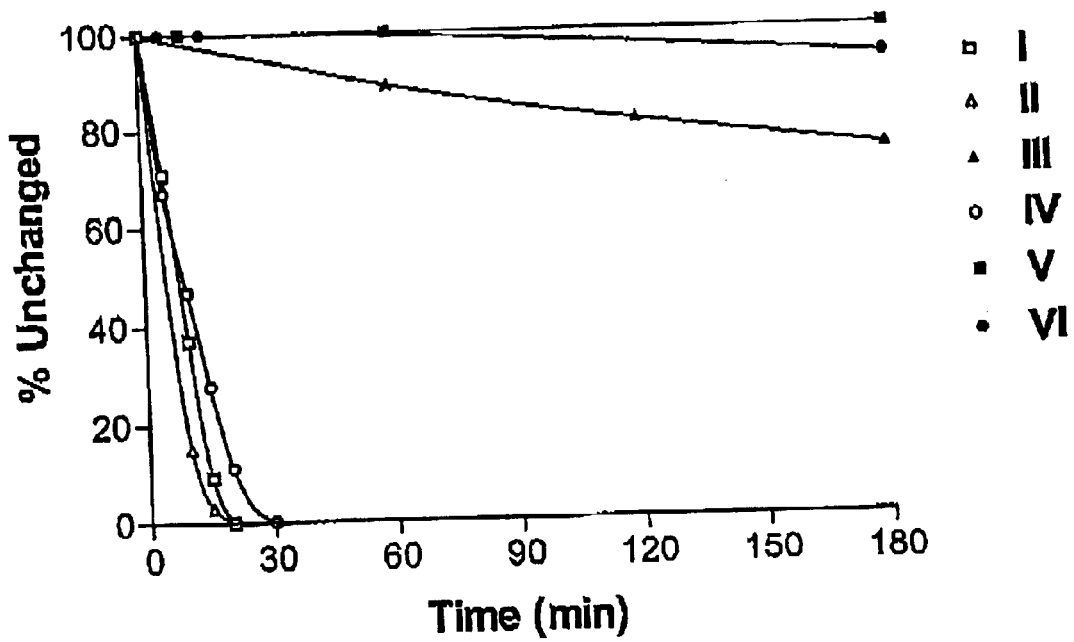
FIG. 5 shows γ-glutamyltranspeptidase mediated hydrolysis of GSH-analogues. Peptide isosteres were incubated with 0.25 mg/ml bovine γ-glutamyltranspeptidase in 0.1M Tris-HCl buffer pH=7.4. At the appropriate time-point a sample (100 μL) was taken, heat inactivated and stored on ice until HPLC analysis. Disappearance of the indicated compounds was determined by RP-HPLC. Open markers indicate γGT sensitive compounds, closed markers are γGT stabilized.

FIG. 5 depicts the hydrolysis of the various GS-EA mimics by γGT.

As expected, the native glutathione-ethacrymic acid conjugated (I) was cleaved rapidly. The chosen conditions resulted in complete degradation of the GSH backbone within 20 minutes ($t_{1/2}$=8 min). Compounds II and IV, each having an unmodified γ-glutamyl peptide bond, are also very sensitive towards γGT mediated cleavage. For these compounds, $t_{1/2}$ was approximately equal to the half-life of GS-EA.

The γ-glutamyl modified compounds (III, V, and VI) all showed greatly improved stability towards γGT. N-methylated compound III was hydrolyzed by γGT, albeit much slower than unmodified γ-glutamyl amides. After prolonged exposure to γGT, urethane VI also underwent minor hydrolysis. The reduced peptide isostere V was completely insensitive towards γ-glutamyl transpeptidase.

Inhibition of rat liver cytosolic GSTs

Freshly isolated rat livers were emulsified in 0.1M KCl using a Potter-Elvehjem homogeniser. After initial centrifugation for 30 minutes at 9000 g, the resulting supernatant was subjected to a second centrifugation for 75 minutes at 10$^5$ g. The cytosolic protein containing supernatant (S100) was used for the GST inhibition experiments. GST inhibition experiments were performed. All solutions were kept on ice until use. Various concentrations of the inhibitions were incubated at 37° C. with rat liver cytosol (1 μl, containing 12 mg of total protein) in sodium-phosphate buffer, pH 6.5, supplemented with 0.1 mM EDTA and 1 mM GSH. Reaction was started by adding 4 μL CDNB in ethanol (final concentration=1 mM, maximal ethanol content=2% v/v). Formation of the GS-CDNB conjugate was followed at 340 nm for 5 minutes. Initial reaction velocities were corrected for the spontaneous (not GST catalyzed) reaction rates. Inhibition was determined as percentage of the non-inhibited reaction rate. Experiments were performed three times with duplicate measurements.

Figure 6:
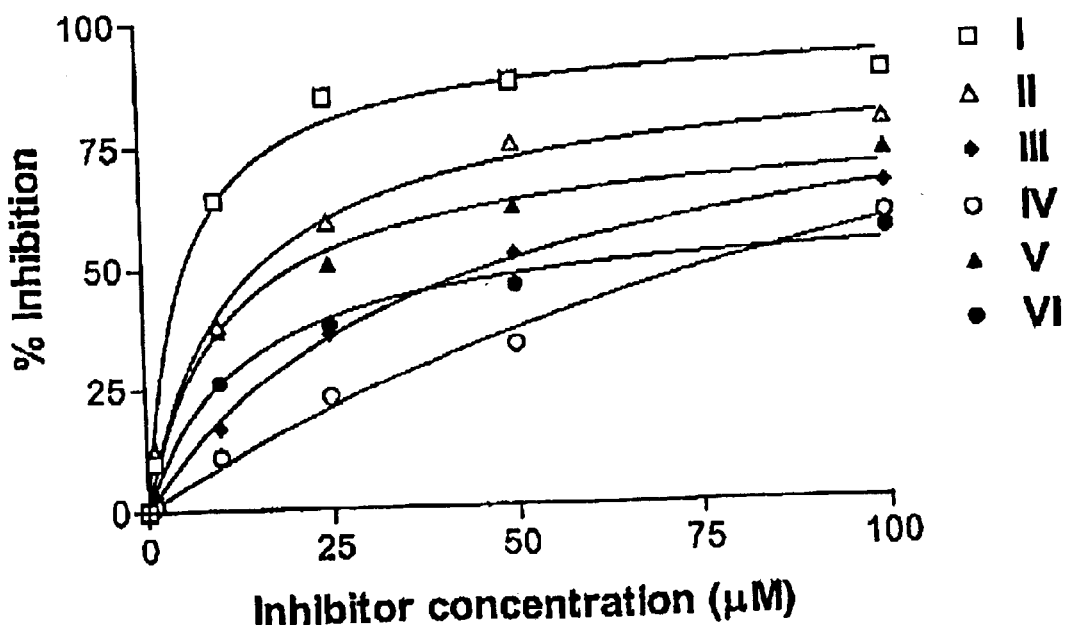
FIG. 6 shows inhibition of rat liver cytosolic GSTs (S100) by GS-EA mimics. Inhibition of GST mediated CDNB-conjugation was tested at pH=6.5, in the presence of non-limiting concentrations of GSH (1 mM) and CDNB (1 mM). The shown data are averages of three separate determinations. For clarity, error-bars were not included. Standard deviations did not exceed 15% of the indicated averages. Open markers with dotted lines indicate γGT sensitive compounds, closed markers with closed lines are γGT stabilized structures.

GST inhibition was tested at six concentrations of the GS-EA mimics. Inhibition profiles of the various inhibitors are shown in FIG. 6.

Rat liver cytosol contains mainly α (1-1, 2-2 and 1-2) and μ (3-3, 4-4, and 3-4) class GSTs. All peptidomimetics were able to inhibit GSH-conjugation by S100 GSTs, indicating that the compounds can be accommodated in the active sites of one or several isoenzymes. Inhibition profiles indicate that most compounds reach a plateau at higher inhibitor concentration, which suggests that not all enzymes are inhibited equally. Disturbing the moieties involved in H-bonding has distinct consequences for enzyme-inhibitor interactions. The GSH-binding site in GST is very tightly suited to accommodate GSH. The binding-capacity of the highly polar GSH-backbone is dictated by its electrostatic complementarity with the enzyme. Certain peptidomimetic changes to the GSH-backbone can therefore result in drastically altered inhibition patterns.

Methylation of the cysteinyl-glycine amide (II) is very well accepted by cytosolic GSTs, indicated by a comparable inhibition pattern to compound I. The cys-gly amide nitrogen is presumably not directly involved in H-bonding. Furthermore, the increased steric bulk can be accommodated within the active site of the GST isoenzymes. Loss of water-bridged interactions may explain the slight decrease in inhibition. The importance of the γ-glutamyl-cysteine amide for enzyme-substrate interactions is clearly seen in compound III. When this peptide bond is methylated, a decrease in inhibition was seen. This may be a result of the loss of a crucial H-bond, or may be a consequence of steric clashes with the enzyme. Compound IV, completely lacking the cysteinyl-glycine peptide bond is a poor inhibitor of cytosolic GSTs. The drop in inhibition is a result of omission of the carbonyl oxygen, which is an important H-bond acceptor. The increased flexibility of the alkyl moiety is probably also an important factor, as enthropic effects may prevent this compound from obtaining its optimal bioactive conformation. Compounds V and VI are efficient γGT stable inhibitors of which the reduced peptide isostere seems to have the most favorable inhibition characteristics.

What is claimed is:

1. A compound of formula

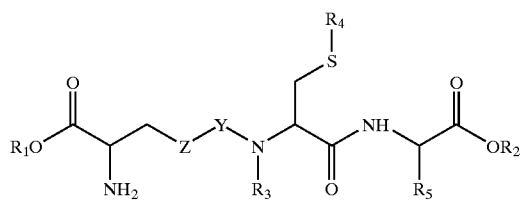

wherein
Z=CH$_2$ and Y=CH$_2$, or
Z=O and Y=CO=O,
R$_1$ and R$_2$ are independently selected from the group consisting of H, linear or branched alkyl (1–25C), aralkyl (6–26C), cycloalkyl (6–25C), heterocycles (6–20C), and ethers or polyethers (3–25C), or R$_1$–R$_2$ together have 2–20C atoms and form a macrocycle with the remainder of formula I;
R$_3$ is selected from the group consisting of H and CH$_3$,
R$_4$ is selected from the group consisting of 6–8C alkyl, benzyl, naphthyl and a therapeutically active compound, and
R$_5$ is selected from the group consisting of H, phenyl, Ch$_3$ and CH$_2$phenyl or a pharmaceutically acceptable salt thereof.

2. The compound of the formula in claim 1 wherein R$_3$ is H.

3. The compound of claim 1 wherein R$_4$ is benzyl.

4. The compound of claim 1 wherein R$_5$ is phenyl.

5. The compound according to claim 1 having formula

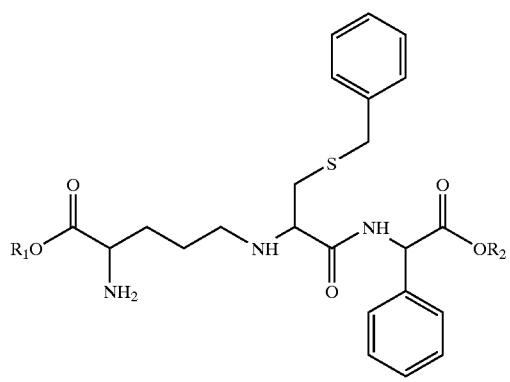

wherein R$_1$ and R$_2$ are the same as defined in claim 1.

6. The compound according to claim 1 having formula

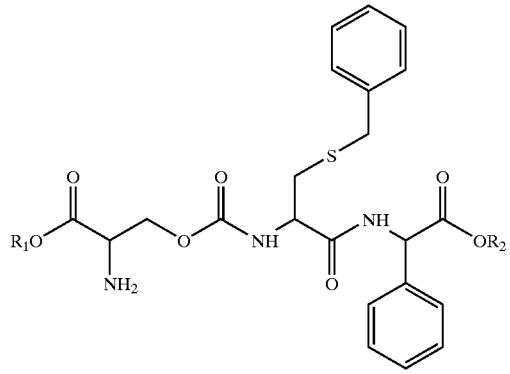

wherein R$_1$ and R$_2$ are the same as defined in claim 1.

7. The compound according to claim 1 having the stereochemistry of formula

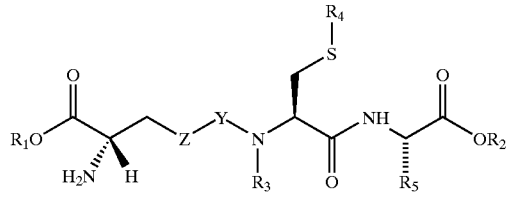

wherein R$_1$–R$_5$ are the same as defined in claim 1.

8. Pharmaceutical composition comprising a compound according to claim 1 together with a pharmaceutically acceptable carrier.

* * * * *